(12) United States Patent
Tanghøj

(10) Patent No.: US 9,205,222 B2
(45) Date of Patent: Dec. 8, 2015

(54) CATHETER ASSEMBLY

(75) Inventor: Allan Tanghøj, Kokkedal (DK)

(73) Assignee: Coloplast A/S, Humlebaek (DK)

( * ) Notice: Subject to any disclaimer, the term of this patent is extended or adjusted under 35 U.S.C. 154(b) by 192 days.

(21) Appl. No.: 13/992,763

(22) PCT Filed: Dec. 16, 2011

(86) PCT No.: PCT/DK2011/050490
§ 371 (c)(1),
(2), (4) Date: Jun. 10, 2013

(87) PCT Pub. No.: WO2012/079590
PCT Pub. Date: Jun. 21, 2012

(65) Prior Publication Data
US 2013/0261608 A1    Oct. 3, 2013

(30) Foreign Application Priority Data
Dec. 17, 2010    (DK) .................................. 2010 70552

(51) Int. Cl.
*A61M 25/00* (2006.01)
*A61M 25/01* (2006.01)
*A61M 25/16* (2006.01)
*A61B 19/02* (2006.01)
(Continued)

(52) U.S. Cl.
CPC .......... *A61M 25/002* (2013.01); *A61B 1/00142* (2013.01); *A61B 1/00144* (2013.01); *A61B 19/026* (2013.01); *A61M 25/0017* (2013.01); *A61M 25/0111* (2013.01); *A61M 25/0113* (2013.01); *A45C 2011/007* (2013.01); *A61M 25/01* (2013.01); *B65D 33/007* (2013.01); *B65D 75/30* (2013.01)

(58) Field of Classification Search
CPC .......... A61M 25/002; A61M 25/0017; A61M 25/0113; A61M 25/0111; A61M 25/01; A61B 19/026; A61B 2019/0274; A61B 1/00142; A61B 1/00144; A61F 2/0095; B65D 77/28; B65D 33/007; B65D 75/30; B65D 75/32; B65D 75/325; B65D 75/321; B65D 75/585; A45C 2011/007; A45C 11/008; A45C 11/32; A45C 2011/322; A45C 11/34; A45C 11/36; A45C 33/005
See application file for complete search history.

(56) References Cited

U.S. PATENT DOCUMENTS 3,098,601 A * 7/1963 Anderson et al. ............. 383/205
3,635,376 A * 1/1972 Hellstrom ..................... 222/107
(Continued)

FOREIGN PATENT DOCUMENTS

EP    0613697    9/1994
EP    0667170    8/1995
(Continued)

*Primary Examiner* — Adam Marcetich
(74) *Attorney, Agent, or Firm* — Coloplast Corp., Coloplast A/S; Nick Baumann

(57) ABSTRACT

A urinary catheter assembly (1) is provided. The catheter assembly has an intermittent urinary catheter (2) with low-friction surface and a tubular elongated package (3) with a side-opening (15). The catheter may be provided with a hydrophilic surface and the package may include a liquid swelling medium. The user may grab the connector (4) through the side-opening and pull out the catheter of the package through there. Spillage of the liquid swelling medium or lubricant is avoided. The side-opening may be configured so that it has two stable configurations, a storing and a folded configuration.

11 Claims, 2 Drawing Sheets

(51) Int. Cl.
*A61B 1/00* (2006.01)
*A45C 11/00* (2006.01)
*B65D 75/30* (2006.01)
*B65D 33/00* (2006.01)

(56) References Cited

U.S. PATENT DOCUMENTS

| | | | |
|---|---|---|---|
| 3,761,013 A | | 9/1973 | Schuster |
| 4,266,667 A | * | 5/1981 | Ishigaki .................. 206/469 |
| 4,379,506 A | * | 4/1983 | Davidson ................ 206/364 |
| 4,838,429 A | * | 6/1989 | Fabisiewicz et al. ...... 383/205 |
| 5,855,435 A | * | 1/1999 | Chiesa .................... 383/204 |
| 6,457,863 B1 | * | 10/2002 | Vassallo ................... 383/43 |
| 2001/0001443 A1 | * | 5/2001 | Kayerod et al. .......... 206/364 |
| 2010/0012668 A1 | * | 1/2010 | Hong ...................... 220/660 |
| 2010/0116772 A1 | * | 5/2010 | Teys ....................... 215/228 |
| 2011/0056852 A1 | * | 3/2011 | Fr jd ...................... 206/210 |
| 2011/0259888 A1 | * | 10/2011 | Kanderka et al. ......... 220/276 |

FOREIGN PATENT DOCUMENTS

| | | |
|---|---|---|
| EP | 2292293 | 3/2011 |
| WO | 03092779 | 11/2003 |

* cited by examiner

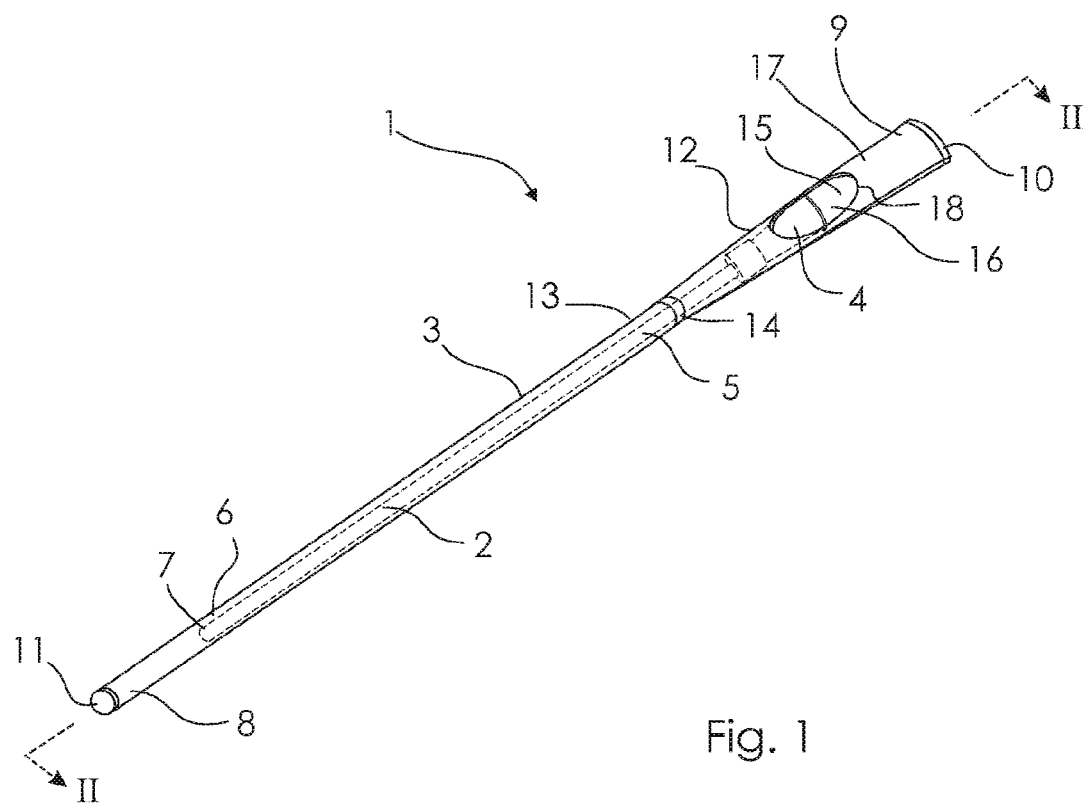
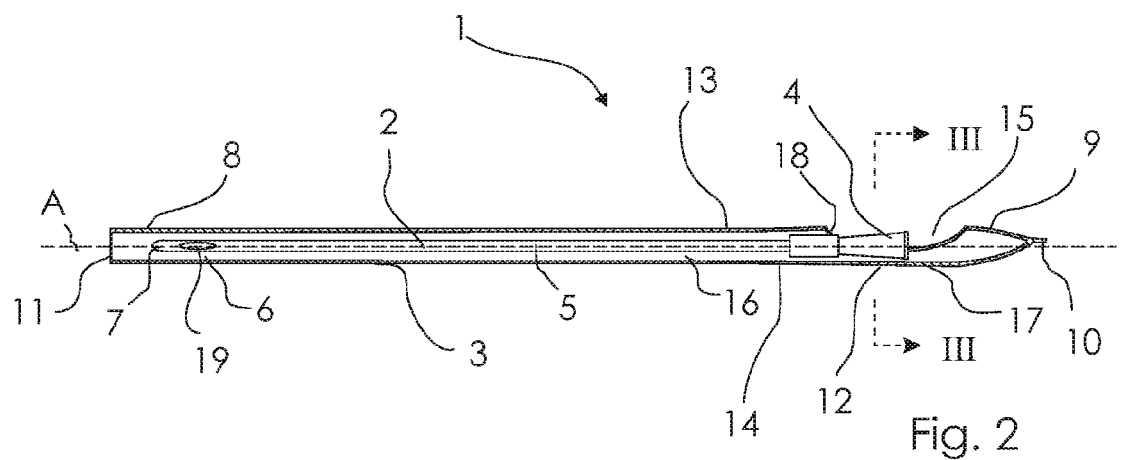
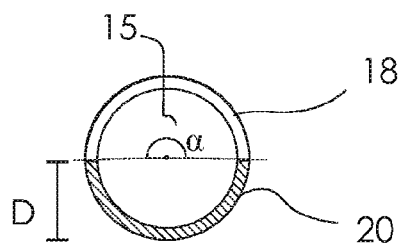
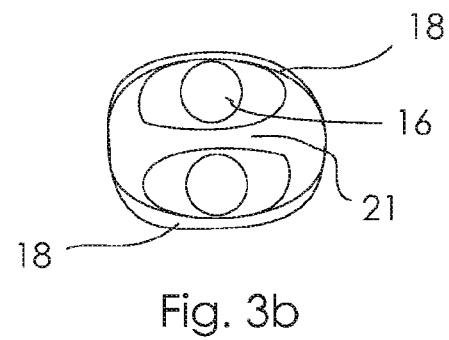

CATHETER ASSEMBLY

The invention relates to a urinary catheter assembly comprising an intermittent urinary catheter and a catheter package comprising an elongated tubular element. The package has a side-opening for removing the catheter.

BACKGROUND

Catheters for draining the urinary bladder are increasingly used for intermittent catheterization. Intermittent catheters are often used by people who suffer from urinary incontinence or by people who have a diminished or no control over voluntary urination, such as para- or tetraplegics and have to use catheters for voiding the urinary bladder.

A number of different variations of intermittent catheter assemblies exist, where the catheter types are typically either hydrogel lubricated catheters or catheters that are provided with a friction reducing hydrophilic surface coating. The choice of catheter assemblies varies from user to user, where some prefer to use a simple catheter assembly, where the catheter is provided in a package and ready to use or only needs activation or lubrication prior to use. Others prefer to use a catheter assembly, where the catheter is provided with a urine bag, so the user does not need access to facilities to dispose of the urine during catheterization but may collect the urine inside the urine bag and dispose of the used assembly subsequently.

DESCRIPTION OF RELATED ART

A recent development within the field intermittent catheters is to provide a ready to use catheter that is discrete and easy to use, as disclosed in e.g. WO 03/002179. However, the majority of intermittent catheter users still use conventional full length catheters for voiding their bladder.

Conventional full length ready to use catheters, such as SpeediCath™, come in catheter packages having at least two layered gas impermeable foils that are welded along the peripheral edges ensuring that the catheter and the hydrophilic swelling agent are maintained in a ready to use condition during the shelf-life of the product. The packages are arranged such that the user has to grab each foil and separate the foils along the welded edge to open the package. In some cases this may be difficult for users that have reduced hand or finger dexterity resulting in the foils being separated more than necessary which may lead to the spillage of the hydrophilic swelling agent that is present in the package.

Another type of catheter assembly is disclosed in WO 00/30575, which is a urinary catheter assembly comprising a urinary catheter and a flexible tubular catheter package, comprising a hose member narrowly surrounding the catheter, where the hose member is opened at the proximal and/or the distal end to allow the retraction of the catheter from the package, and where parts of the package may be used as an applicator for inserting the catheter. When this package is used as a ready to use catheter assembly, the hose member is filled with a hydrophilic swelling medium, which has to be drained from the package prior to use in order to reduce the risk of spillage during use.

SUMMARY OF THE INVENTION

This invention concerns an intermittent urinary catheter assembly having an intermittent urinary catheter stored in a package. The package is made of a tubular material and is provided with a side opening for removing the catheter from the package. The side-opening provides an advantage, when liquid or hydrogel is stored in the package, because it allows the user to remove the catheter without spilling the stored content. Furthermore, it provides a pre-defined opening, which ensures that the package is only opened there.

DETAILED DESCRIPTION OF THE INVENTION

In a first aspect, the invention relates to an intermittent urinary catheter assembly comprising: an intermittent urinary catheter comprising a catheter tube having a proximal end and a distal end, where the proximal end comprises a catheter tip and the distal end comprises a catheter connector, and a catheter package for accommodating the intermittent urinary catheter wherein the package is of a general elongate shape having a proximal end and a distal end and is made of a tubular material, where the package comprises a cavity for accommodating at least the insertable part of the catheter tube, wherein the catheter package is provided with an opening arranged in a predefined area in a side wall of the tubular material for allowing the extraction of the catheter from the package.

A urinary catheter assembly as described has the advantage that the predefined area in the side wall of the tubular material is prepared in such a way that the catheter may be extracted from the catheter package via the predefined opening area, ensuring that the user does not involuntarily damage the package during opening, resulting in spillages of lubricant or hydrophilic swelling medium. The predefined opening area ensures that the package is opened in the manner intended by the manufacturer of the package, and the risk of spillage of the stored contents and contamination of the catheter is reduced significantly.

In the following, whenever referring to a proximal end of an element of the invention, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted. The same definitions apply to the package—the proximal end is the end storing the proximal end of the catheter and the distal end is the opposite end.

The longitudinal direction is the distal to the proximal end. The transverse direction is the direction perpendicular to the longitudinal direction, which corresponds to the direction across the shaft of the catheter.

The catheter described in this application is to be used as an intermittent urinary catheter.

The catheter comprises a main tubular part with an inner lumen extending from the distal end to the proximal end. The tip is positioned in the proximal end of the catheter and is provided as a rounded closed end of the tube constituting the main part of the catheter. The catheter is provided with one or more eyelets which allow urine to pass from the external surface of the catheter tube to the inner lumen of the catheter. The catheter may comprise a connector in the distal end and may in an embodiment comprise a flared end of the catheter so that the diameter of the connector increases with respect to the tubular part. The catheter may also comprise a handle in the distal end, which has a length allowing the user to manipulate the catheter.

Usually catheters are from size 6 FR to size 24 FR.

Catheters of this invention may prior to use be provided with a hydrophilic coating so as to impart a low-friction insertion. The hydrophilic coating may be provided only on the insertable part of the catheter. The hydrophilic surface coating is of the kind which, when hydrated or swelled using a swelling medium, reduces the friction on the surface area of the catheter which is intended to be inserted into the urinary channel of a user corresponding to the insertable part of the catheter.

An intermittent hydrophilic catheter differs from an indwelling catheter in that the hydrophilic surface coating of such a catheter is not suitable for indwelling use, because the surface coating tends to stick inside the mucosa of the urethra if left inside the body for a period exceeding 5-20 minutes, due to the hydrophilic coating transforming from being highly lubricious when fully wetted (95% weight water) to being adhesive when the hydration level of the coating is reduced (<75% weight water).

In the present invention, the term "predefined area in a side wall" means that the opening is positioned in an area that is radial to an axis defined by the longitudinal axis of the package when extended. The predefined area in the side wall may be seen as being proximal to the distal end of the tubular member and distal to the proximal end of the tubular member, meaning that the opening does not comprise the distal or proximal ends of the tubular member. Another way of describing it is that the opening is a side-opening.

In one embodiment of the present invention, the catheter package may comprise a medium for activating the hydrophilic surface coating of the catheter. The activating medium may be a water based substance, such as sterile water, saline-solution, or any water based liquid. Furthermore, the activating medium may be in the form of a vapour contributing material, such as a wetted sponge, woven or non-woven material comprising a vapour contributing liquid. By introducing a vapour contributing material into the package, the vapour will over time hydrate the hydrophilic coating ensuring that the coating is activated and that the hydrophilic coating provides a low-friction surface for the catheter.

In one embodiment of the present invention, the tubular material of the package may have walls made of gas impermeable material. Such an embodiment may be advantageous where the package contains a hydrogel lubricated catheter, ensuring that the hydrogel does not dry out over the lifetime of the catheter assembly. Furthermore, the gas impermeable material of the package is advantageous in case the catheter assembly is provided as a ready-to-use catheter assembly, where the catheter is provided with a hydrophilic surface coating and the coating is activated upon or subsequent to the production of the assembly. A ready-to-use catheter assembly of that kind requires that the hydrophilic surface coating is activated during the production process of the catheter assembly and is maintained activated at least during the shelf-life of the product. The gas-impermeable material of the package is used to ensure that the liquid or vapour swelling medium contained in the package does not evaporate from the package and maintains the catheter in a ready to use state. The gas impermeable material for the package or the side walls of the package may be of the kind disclosed in Danish patent applications PA 2010 70351 and PA 2010 70350, which are hereby incorporated by reference.

In one embodiment of the present invention, the opening in the side wall of the package may be a through-going opening in the package, where the material of the predefined area has been removed from the side wall of the package, by cutting, stamping, welding, and so on. Thus, the through-going opening may therefore be the boundary that determines the predefined area to which the user may extract the catheter.

In one embodiment of the present invention, the opening in the predefined area may be a weakening line along the periphery of the predefined area. This means that the opening is defined by the weakening line, and when the user intends to remove the catheter from the package, the user may assert pulling or pushing force to the material inside the area that is defined by the weakening line, allowing the weakening line to separate the material from the tubular member or the package.

The through-going opening, as described above, may be closed by a releasable flap. The releasable flap may be fixed to the package during manufacturing and ensures that the contents of the catheter package are maintained inside the catheter package during storage. The releasable flap may be attached to the periphery of the through-going opening at the outer surface of the tubular member and/or surrounding areas, depending on how the flap is to be released. The flap may be of a liquid- and gas-impermeable material ensuring that when the flap is fixed to the package in its closed position, any liquid or lubricant arranged inside the package will not evaporate through the flap. Thereby, the catheter is kept lubricated or for hydrophilic catheters, hydrated inside the package throughout the shelf-life of the catheter assembly.

The releasable flap may alternatively be adhesively fixed to the package when the package is in its closed position, or maintained fixed to the package in any suitable way. The seal between the flap and the package may be liquid and gas impermeable, ensuring that liquids or gasses do not escape from the package, when closed, in the sealing area between the flap and the package.

The releasable flap may be attached to the package by means of having at least two different attachment strengths, so that when the flap is pulled by the user, a part of the flap will release from the package while another part of the flap will remain in place. This means that when the user opens the package by pulling one end of the flap, the attachment means that is close to the end being pulled is attached with a lower strength than the opposite end. This ensures that when the flap is pulled off the opening of the package, the opposite end will remain attached to the package. The attachment strength of the releasable area of the releasable flap may be in the range of 1-20N, meaning that if the flap is pulled with such a force in a direction away from the package, the predefined releasing area of the flap will allow the flap to separate from the package. The permanent attachment area of the flap may be of a strength in the range of more than 20N, meaning that even though the flap is pulled with considerable force, the permanent attachment area of the flap will not separate from the package, and the flap will remain attached to the package. In a different embodiment, the flap may be attached to the package in such a way that the entire flap will release from the package when pulled off the package, i.e. having the entire attachment area arranged as a releasable area.

The opening in the catheter package may be provided in the form of a closed line shape, where the opening, when the catheter package has been opened by the user, is an area in the side wall where a portion of material has been removed from the side wall, to allow access to the internal cavity of the catheter package or the tubular member. The closed line shape may include a circle, an ellipse, an n-shaped polygon (n>2) or any other suitable shape for the opening.

In one embodiment of the present invention, the opening in the catheter package may further be provided with a slit, which allows the peripheral walls of the opening to be folded away from the predefined shape of the opening, where the slit ensures that the material of the side wall does not constrict the folding away of the peripheral walls.

In one embodiment of the present invention, the opening in the catheter package is arranged so that the tubular member may be folded from the longitudinal axis of the tubular member across the cross sectional area of the tubular member that comprises the opening. This means that a portion of the tubular member may be folded backwards to allow an improved access to the catheter arranged inside the package. This means that the extraction of the catheter from the package will be easier for the user, as the folded portion will expose the internal lumen of the tubular member via the opening, and the user may grab the catheter via e.g. its connector along the longitudinal axis of the catheter package or tubular member.

In one embodiment of the present invention, the opening in the catheter package defines an area of the tubular member where the material is removed from the side wall of the tubular member over an area defining more than 180 degrees of a cross sectional area of the tubular member. This means that when looking at a cross sectional cut of the tubular member, the opening is cut into an area of more than 50% of the viewed cross section. Thus, when the package is opened, and the tubular member is folded or bent from its longitudinal axis, the bent or folded part will snap into place across the remaining material which is less than 50% of the viewed cross sectional area, due to the curvature of the tubular member. The curvature of the tubular member will thus be inverted during the folding and the inverted curvature will ensure that the fold does not snap into its original unfolded position, but will stay in its substantially folded position. This means that the opening in the side wall of the catheter package will provide a bi-stable portion, allowing a portion of the tubular member to be maneuvered from its longitudinal axis, the remaining portion thus defining the longitudinal axis, into a fold which is stable in its folded position. Subsequently, the folded portion may be maneuvered back towards the longitudinal axis of the tubular member and maintain its position there. This bi-stable arrangement allows the tubular member to be moved into and from its folded position according to the user's needs.

In one embodiment of the present invention, the tubular member may be provided with an openable closure at one end which is distal to the opening of the catheter package. This means that when the catheter is removed from its package, the catheter connector may be inserted into the opening in the side wall of the tubular member. Upon opening the end closure, the tubular member may be used as an extension to the catheter. Thus, when the user inserts the catheter into the urethra and urinary bladder, and drains the bladder, the urine will flow through the catheter and into the tubular member via the catheter connector which is inserted into the opening of the package. The openable closure at one end of the package will allow the urine to flow from the end portion of the package, when the closure has been opened. While the catheter assembly is in its storage state, the openable closure is liquid- and gas-impermeably closed along with the remaining parts of the package, so that the contents of the package is protected from contamination from outside sources. This ensures that the contents of the package cannot escape from the package via evaporation or leakage.

In one embodiment of the present invention, the catheter may be arranged inside the catheter package having the catheter connector aligned with the opening, along the longitudinal axis of the catheter package. This means that when the package is opened, the user may have access to the catheter connector via the opening in the side wall of the tubular member. Thus, the user may grab the connector directly, and remove the catheter from the package while grabbing the connector without having to come into contact with the insertable part of the catheter. Thereby, the risk of contaminating the catheter during extraction is minimized.

In one embodiment of the present invention, the catheter connector may be fixed in a position relative to the opening of the catheter package. This means that when the user opens the package, the catheter connector may remain in an optimal position relative to the opening allowing the user to access the connector in an optimal manner. This reduces the risk that the connector will move, relative to the opening, during production and/or storage of the catheter assembly. When the catheter assembly is to be used, the connector will be positioned such that the user may easily access the connector via the opening. If the connector and/or the catheter moves inside the package during the production and/or storage of the catheter assembly, the connector may move into a position where the user might have difficulty accessing the connector via the opening of the package. The user may then have to perform additional maneuvering of the package to get the connector into an extractable position. By fixing the catheter connection in position it is ensured that the connector will maintain its position during storage, production and/or use, so that the user will know that he or she will not have difficulty in extracting the catheter from its package.

In one embodiment of the present invention, the tubular member may be provided with an area of the package having a cross sectional area that is larger than the cross sectional area of the remaining parts of the package. This large cross sectional area may be arranged to accommodate the catheter connector, which conventionally has a larger outer diameter than the remaining parts of the catheter. This means that the inner surface diameter of the package or the tubular member may be kept slightly larger than the insertable part of the catheter. Thereby, in case the catheter is a hydrophilic catheter, the amount of swelling medium may be kept at a minimum without having to risk that the hydrophilic catheter will dry out during storage.

In one embodiment of the present invention, one portion of the external surface of the catheter connector may have a cross sectional area that is equal to or larger than one portion of the cross sectional area of an internal surface of the tubular member. The catheter comprising the catheter connector may be arranged inside the package where the catheter connector and the internal surface of the tubular member provide a liquid tight seal. This means that when the catheter assembly is produced, and the catheter is arranged inside the package, a swelling medium, for hydrophilic catheters, may be arranged on one side of the liquid tight seal. The part of the catheter and/or connector that is arranged on the opposite side of the liquid tight seal may be kept in a substantially dry state. The advantage of this arrangement is that the user may grab on to a dry catheter connector, where no swelling medium or gel will contaminate the user's fingers, thus maintaining a higher cleanliness during the extraction and/or use of the catheter.

BRIEF DESCRIPTION OF THE DRAWING

FIG. 1 illustrates a perspective view of a catheter assembly according to the present invention.

FIG. 2 illustrates a cross sectional view of a catheter assembly as in FIG. 1 across II-II in FIG. 1.

FIG. 3 illustrates a cross sectional view of a catheter assembly as shown in FIG. 2 taken across axis III-III.

DETAILED DESCRIPTION OF THE DRAWING

Figure 4A:
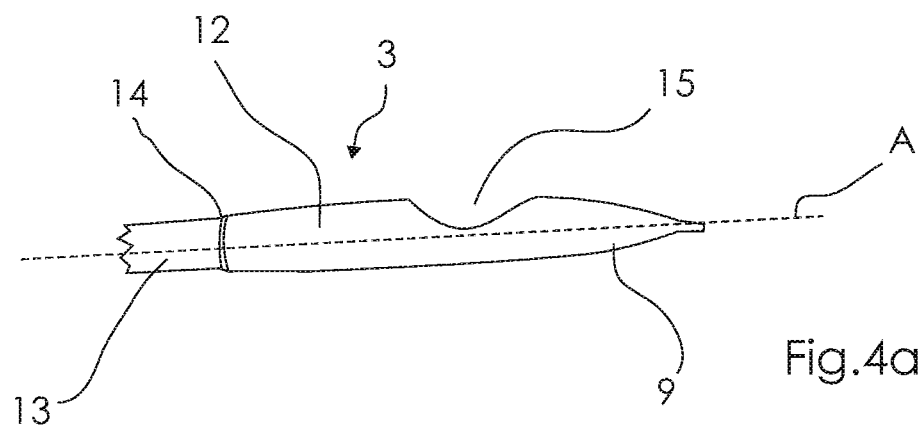
FIGS. 4a and 4b illustrate one end of a catheter assembly in an unfolded and folded position, respectively.

FIG. 1 shows a perspective top view of a catheter assembly 1 according to one embodiment of the present invention, where the catheter assembly 1 comprises a catheter 2 and a catheter package 3, where the catheter 2 is arranged inside the catheter package 3. The catheter 2 comprises a catheter connector 4 and a catheter tube 5, where the proximal end 6 of the catheter tube 5 comprises an insertable catheter tip 7, which closes off the internal lumen of the catheter tube 5. The catheter tube 5 has at least one eyelet (not shown, 19, FIG. 2) in the side wall to allow urine to enter the internal lumen of the catheter tube 5.

The catheter 2 is arranged inside the catheter package 3, where the package 3 is made of a tubular material having a proximal end 8 and a distal end 9. During production, the distal end 9 may be closed using a welding 10, that welds the side wall of the distal end 9 together to provide a liquid and gas impermeable closure. During production, the proximal end 8 of the catheter package 3 is in this embodiment closed using an openable closure 11, which in its closed state, during packing and storage, provides a liquid and gas impermeable closure, and in its open state, during use, provides an opening into the internal lumen of the catheter package 3, allowing the contents of the catheter package 3 to be drained from the package 3.

The catheter package 3 is formed from a tubular member, where a distal part 12 of the package 3 may have an increased diameter, in order to allow the catheter connector 4 to fit inside the package 3, while a proximal part 13 of the catheter package 3 has a cross sectional diameter that is smaller than the diameter of the distal part 12, so that the proximal part 13 has an internal diameter that is slightly larger than the outer diameter of the catheter tube 5. The increase in diameter between the proximal 13 and the distal part 12 may occur over a junction 14, where the junction 14 may ensure that the catheter connector may not be maneuvered in a proximal direction past the junction 14.

An opening 15 may be provided in the distal part 12 of the catheter package 3, where the opening provides an access from the outside into the internal lumen 16 of the catheter package 3. The opening 15 may be cut out of the side wall of the catheter package 3, creating a well defined opening 15, which has a peripheral edge 18 that defines the opening 15. Prior to using the catheter, a user may grip the catheter connector 4 and pull the catheter 2 via its connector 4 from its package 3 through the opening 15 in the side wall 17 of the catheter package.

FIG. 2 shows a cross sectional view of the catheter assembly in FIG. 1, where the eyelet 19 of the catheter 2 is shown close to its proximal end 6.

FIG. 3a shows a cross sectional view of the catheter package in FIG. 2, where the peripheral edge 18 of the opening 15 is cut into the side wall 20 of the catheter package 3. It may be preferred that the opening is cut into the side wall 20 in such a way that the material cut out of the opening is more than 50% percent of the circumference of the catheter package, leaving the side wall material which is less than 50% of the diameter as shown by measurement D. This means that the material removed, defines a cross sectional area that is in excess of 180 degrees, as shown by angle α. By removing the more than 50% of the material, the distal end 9 of the catheter package may be folded away from the longitudinal axis A (FIG. 2) of the catheter package, at the point where most material has been removed from the side wall of the package, allowing the side wall to fold upon itself creating a bi-stable fold 21 of the catheter package, as shown in FIGS. 3b and 4b.

FIG. 4a shows the distal part 12 of the catheter package 3, where the distal part 12 houses the catheter connector (not shown). In this figure, the distal part 12 is in its unfolded configuration, where the opening 15 is arranged in the side wall of the package 3 and the distal end 9 of the catheter package is arranged along the longitudinal axis A of the catheter package.

Figure 4B:
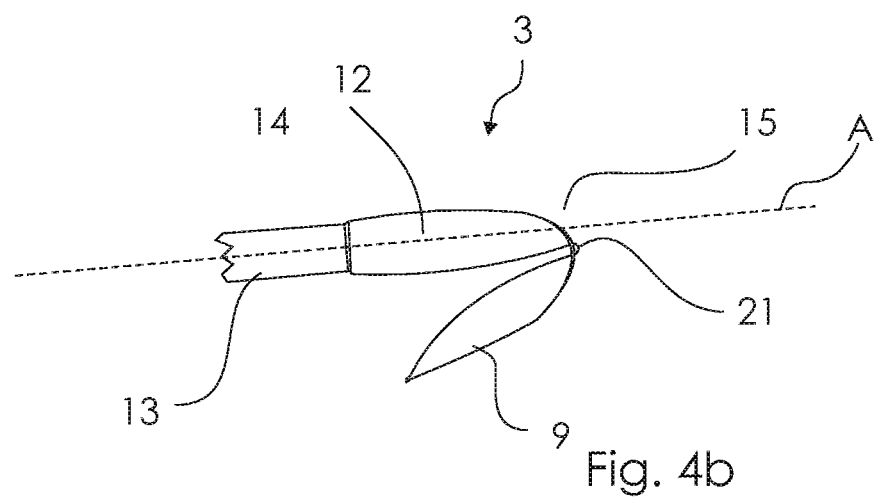

FIG. 4b shows when the distal end 9 of the catheter package has been pushed or pulled away from the longitudinal axis A and the distal end has been bent or folded backwards, in a direction away from the opening 15. When the opening defines an area where more than 180 degrees of material has been removed, as shown in FIG. 3a, the side walls fold outwards and lock the distal end 9 in its folded position, away from the longitudinal axis A. The folding of the distal end 9 allows the user to get an easier access to the catheter connector, which is located inside the inner lumen of the catheter package 3. The user may easily grip or access the catheter connector and pull the catheter out of the package in a direction away from the package along the longitudinal axis of the package.

Figure 5:
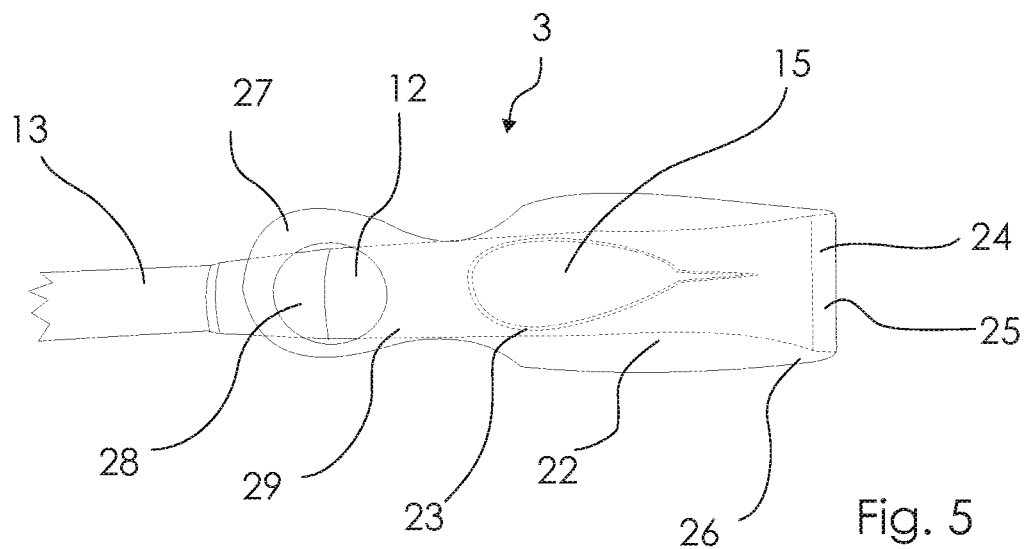
FIG. 5 illustrates a catheter assembly having a removable flap.

FIG. 5 is a top view of the proximal part 12 of the catheter package 3. The proximal part has been arranged with a releasable flap 22, which closes the opening 15 of the package and is attached to the package around the periphery of the opening 15. The releasable flap 22 may be attached to the package using a first attachment means 23 and a second attachment means 24. The first attachment means 23 is the attachment of the flap to close the opening 15 to ensure that the package 3 is liquid- and gas-impermeable, while the second attachment means 24 attaches the flap 22 along a hinge-like attachment 25 located at the distal end 26 of the flap 22. The latter ensures that when the flap has been removed from the periphery of the opening 15, the second attachment means ensures that the flap is not completely removed from the package, and maintains its attachment along its hinge-like attachment 25 at the distal end 9 of the catheter package 3.

The removable flap 22 may be provided with a gripping means 27 which is on the proximal end 29 of the flap, and where the proximal end 29 of the flap is not attached to the package 3, allowing the proximal end of the flap 22 to be pulled away from the surface of the package 3, without exercising a substantial force. The gripping means 27 may be in the form of an enlarged portion or as shown in FIG. 5 in the form of an opening 28 in which the user may insert a finger, in order to pull the releasable flap 22 from the package in a radial direction away from the package.

The invention claimed is:

1. An intermittent urinary catheter assembly comprising:
   an intermittent urinary catheter comprising a catheter tube having a proximal end and a distal end, where the proximal end comprises a catheter tip and the distal end comprises a catheter connector; and
   a catheter package, with the intermittent urinary catheter disposed in the catheter package, wherein the catheter package is a tube having an outside diameter and a tube circumference, with the catheter package having a proximal end portion with a circular cross-sectional shape sized to retain the catheter tube and a distal end portion with a non-circular cross-sectional shape sized to retain the catheter connector;
   wherein the catheter package is provided with an opening formed through more than half of the tube circumference of a wall of the tube, with the opening located between the proximal end and the catheter connector of the intermittent urinary catheter;
   wherein a remaining portion of the wall of the tube at the opening provides the catheter package with a bi-stable fold region configured to allow the catheter package to provide a stable folded open position.

2. The intermittent urinary catheter assembly according to claim 1, wherein the intermittent urinary catheter is provided with a hydrophilic surface coating.

3. The intermittent urinary catheter assembly according to claim 1, wherein the tube is formed of gas impermeable material.

4. The intermittent urinary catheter assembly according to claim 1, wherein the opening is formed by a weakening line along a portion of the tube circumference.

5. The intermittent urinary catheter assembly according to claim 1, further comprising a releasable flap provided over the opening.

6. The interittent urinary catheter assembly according to claim 5, wherein the releasable flap has two different attachment strengths.

7. The intermittent urinary catheter assembly according to claim 1, wherein the tube has an openable closure distal to the opening of the catheter package.

8. The intermittent urinary catheter assembly according to claim 1, wherein the catheter connector is substantially aligned with the opening.

9. The intermittent urinary catheter assembly according to claim 1, wherein the catheter connector is fixed in position relative to the opening of the catheter package.

10. The intermittent urinary catheter assembly according to claim 1, further comprising:
   a junction formed at a location between the proximal end portion and the distal end portion of the catheter package, with the junction provided to prevent movement of the catheter connector in a proximal direction away from the junction toward the proximal end portion of the catheter package.

11. An intermittent urinary catheter assembly comprising:

an intermittent urinary catheter comprising a catheter tube having a proximal end and a distal end, where the proximal end comprises a catheter tip and the distal end comprises a catheter connector; and a catheter package, with the intermittent urinary catheter disposed in the catheter package, wherein the catheter package is tubular, with the catheter package having a proximal end portion with a cross-sectional shape sized to retain the catheter tube and a distal end portion with a cross-sectional shape sized to retain the catheter connector, with a diameter of the cross-sectional shape of the proximal end portion smaller than a diameter of the cross-sectional shape of the distal end portion;

wherein the catheter package is provided with an opening formed through more than half of a circumference of a wall of the distal end portion of the catheter package;

wherein a remaining portion of the wall of the distal end portion of the catheter package at the opening provides the catheter package with a bi-stable fold region configured to allow the catheter package to provide a stable folded open position;

wherein a junction is formed at a location between the proximal end portion and the distal end portion of the catheter package, with the junction provided to prevent movement of the catheter connector in a proximal direction away from the junction toward the proximal end portion of the catheter package.

* * * * *